United States Patent [19]

Colodney

[11] 4,058,595

[45] Nov. 15, 1977

[54] STABILIZED TOOTHPASTES CONTAINING AN ENZYME

[75] Inventor: Daniel Colodney, Green Brook, N.J.

[73] Assignee: Colgate-Palmolive Company, New York, N.Y.

[21] Appl. No.: 453,360

[22] Filed: Mar. 21, 1974

Related U.S. Application Data

[63] Continuation of Ser. No. 188,993, Oct. 13, 1971, abandoned.

[51] Int. Cl.² .............................................. A61K 7/38
[52] U.S. Cl. ................................................... 424/50
[58] Field of Search ............................ 424/49, 58, 50

[56] References Cited

U.S. PATENT DOCUMENTS

| | | | |
|---|---|---|---|
| 3,325,364 | 6/1967 | Merritt et al. | 424/94 |
| 3,696,191 | 10/1972 | Weeks | 424/50 |

OTHER PUBLICATIONS

Dixon et al., *Enzymes,* published by Academic Press, New York, 1958, pp. 45, 153 and 493.
McConn et al., *J. Biological Chemistry,* vol. 239, pp. 3706–3715, Nov. 1964.

*Primary Examiner*—Joseph P. Brust
*Attorney, Agent, or Firm*—Steven J. Baron; Murray M. Grill; Herbert S. Sylvester

[57] ABSTRACT

Toothpastes having cosmetic and enzymatic stability containing a neutral protease of *B. subtilis,* a partially hydrolyzed protein, and a Group IIA metal ion.

9 Claims, No Drawings

STABILIZED TOOTHPASTES CONTAINING AN ENZYME

This is a continuation, of application Ser. No. 188,993 filed Oct. 13, 1971 now abandoned.

The present invention relates to improvements in oral and dental hygiene. More specifically, the invention relates to stabilized toothpastes containing a neutral protease of *Bacillus subtilis* (hereinafter referred to as the neutral protease). It has been surprisingly found that this enzyme can be stabilized by the incorporation of controlled amounts of a dual component stabilizing system consisting of a partially hydrolyzed protein and a Group IIA metal ion.

It has been demonstrated by a number of investigators that cetain proteolytic enzymes retard plaque and calculus formation. Thus, it is highly desirable to incorporate these enzymes into cosmetically acceptable toothpaste vehicles. However, it is difficult to formulate enzyme toothpastes since the enzyme becomes progressively inactivated and thus the toothpastes lack the shelf life necessary to be commercially acceptable products.

This invention, however, advantageously provides novel enzymatic toothpastes which are stable.

Other advantages and improvements will become apparent from the following specification.

In general, this invention comprises dentifrice compositions which contain an effective amount of the neutral protease having an activity of at least about 0.02 Anson units per gram of formulation, about 0.1 to 5.0 percent of a partially hydrolyzed protein, and about 0.05 to 2.0 percent of a Group IIA metal ion salt.

Typically, the neutral protease is employed in the toothpastes of this invention in an effective amount of at least about 0.05 percent up to about 1.0 percent, preferably about 0.1 to 0.5 percent and most preferably about 0.25 percent, by weight of the total composition. Effective preparations of the neutral protease have an activity of at least about 0.02 to 0.05 Anson units, preferably about 0.04 Anson units per gram of formulation.

The neutral protease is prepared from *Bacillus subtilis* by the method set forth in U.S. Pat. No. 3,031,380, dated Apr. 24, 1962 which patent is incorporated herein by reference. The neutral protease is protease-amylase mixtures of varying ratios, typically 4 parts protease (pH 7), 1 part protease (pH 10), and 1 part amylase. The average molecular weight of the neutral protease ranges from about 25,000 up to about 40,000.

The dentifrice compositions of this invention contain as the enzyme substrate a partially hydrolyzed edible protein or an edible protein. For the purposes of this invention the partially hydrolyzed or edible protein may be selected from such materials as partially hydrolyzed gelatin, partially hydrolyzed casein, and partially hydrolyzed collagen. The partially hydrolyzed products may be obtained by water, acid, alkali, heat, pressure, or enzymatic degradation. The protein generally has an average modecular weight ranging from about 10,000 up to about 300,000 and preferably about 100,000 and is preferably present in an amount of about 0.1 to about 1.0 to about 1.0 percent, most preferably about 0.5 percent, by weight of the total composition. Particularly suitable proteins are sodium caseinate, calcium caseinate, NZ amine type AT (casein hydrolysate supplied by Sheffield Laboratories), WSP X-1000 (polypeptide derived via collagen hydrolysis supplied by Wilson Pharmaceutical and Chemical Corporation), and Bactopeptone (polypeptide derived via protein hydrolysis supplied by Difco Laboratories).

The toothpastes of this invention also contain a Group IIA metal ion which may be conveniently supplied as a water-soluble, nontoxic salt. Examples of suitable salts include beryllium, magnesium, calcium, strontium and barium chlorides, sulfates, citrates, acetates, glycerol phosphates, glucoheptanates, gluconates, lactates, lactophosphates, lactobionates, and levulinates. The preferred salt is calcium chloride. The salt is preferably present in an amount of about 0.1 to 1.0 percent, most preferably about 0.5 percent, by weight of the total composition.

The stabilized toothpastes of this invention may contain various adjuvants in suitable amounts provided these adjuvants do not substantially adversely affect the desired results.

The instant toothpastes normally have a pH of about 6.5 to 8.5. If desired, the pH may be maintained with a buffering system.

The carrier material of the instant toothpastes contains a substantially water-insoluble polishing agent which is compatible with the formulation. Particularly compatible materials include, for example, dicalcium phosphate dihydrate, dicalcium phosphate anhydrous, tricalcium phosphate, magnesium carbonate, calcium carbonate, calcium pyrophosphate, calcium sulfate, polymethylmethacrylate, bentonite, etc., and suitable mixtures thereof. Abrasive resinous substances such as the condensation products of melamine and urea with formaldehyde can also be used. It is preferred to use dicalcium phosphate dihydrate, dicalcium phosphate anhydrous, and calcium carbonate. The polishing agent may be the sole carrier material and is present in an amount up to about 95 percent of the carrier and generally about 20 to 75 percent of the carrier.

In toothpaste formulations the liquids and solids should necessarily be proportioned to form a creamy mass having the desired consistency which is extrudable from a pressurized container or a collapsible tube (for example, aluminum or lead). In general, the liquids in the toothpaste will comprise chiefly water, glycerine, aqueous solutions of sorbitol, propylene glycol, polyethylene glycol 400, etc., and suitable mixtures thereof. It is advantageous usually to use a mixture of both water and a humectant or binder such as glycerine or sorbitol. The total liquid content will generally be about 20 to 75 percent of the carrier. The amount of water is generally about 10 to 25 percent, preferably about 12 to 17 percent of the carrier. It is preferred to also use a gelling agent in toothpastes such as the natural and synthetic gums and gum-like materials such as Irish moss, gum tragacanth, sodium carboxymethylcellulose, polyvinylpyrrolidone, starch, and the like, usually in an amount up to about 10 percent, and preferably about 0.2 to 5 percent, of the carrier.

A compatible organic surface-active agent may be used in the carrier of the present invention to assist in achieving thorough and complete dispersion of the instant compositions throughout the oral cavity and to render the instant compositions more cosmetically acceptable. The organic surface-active material may be anionic or nonionic in nature; it is preferred to employ as the surface-active agent detersive material which imparts to the composition detersive and foaming properties. Particularly suitable detergents are water-soluble salts of higher fatty acid monoglyceride monosulfates, such as the sodium salt of the monosulfated monoglyceride of hydrogenated coconut oil fatty acids; alkyl aryl sulfonates; higher alkyl sulfoacetates; N-substituted lower alkyl $C_{12}$–$C_{18}$ fatty acid sulfoacetamides; higher fatty acid ester of 1,2 dihydroxy opane sulfonates; higher fatty acid amides of taurine; and fatty acid esters of isothionic acid. The preferred detergent is N-2 ethyl laurate potassium sulfoacetamide.

Other suitable surface-active materials include non-ionic agents such as condensates of sorbitan monostearate with approximately 60 moles of ethylene oxide, condensates of propylene glycol ("Pluronics"), condensates of higher fatty alcohols such as tridecyl alcohol with ethylene oxide, condensates of alkyl thiophenols with 10 to 15 ethylene oxide units, and ethylene oxide addends of monoesters of hexahydric alcohols and inner esters thereof such as sorbitan monolaurate, sorbitol monooleate, and mannitan monopalmitate.

It is preferred to use the surface-active agent in an amount of about 0.05 to 5 percent of the carrier.

Various other materials may also be incorporated into the carrier. Examples thereof are coloring or whitening agents (for example, titanium dioxide), preservatives (for example, sodium benzoate), silicones, chlorophyll compounds, ammoniated materials such as urea, diammonium phosphate, and mixtures thereof, alcohol, menthol, and other constituents. These adjuvants are incorporated into the instant compositions in amounts which do not substantially adversely affect the properties and characteristics and are suitably selected and used in proper amount depending upon the particular type of preparations involved.

It may be desirable also to include antibacterial agents in the carrier, typically in an amount of about 0.01 to 5 percent, preferably about 0.05 to 1.0 percent of the carrier. Typical antibacterial agents include the bisphenols and bis-biguanides such as:
p-chlorophenyl biguanide;
4-chlorobenzhydryl biguanide;
4-chlorobenzhydrylguanylurea;
1,6-di-p-chlorophenylbiguanidohexane
5,6-dichloro-2-guanidinobenzimidazole;
5-amino-1,3-bis(2-ethylhexyl)-5-methylhexahydropyrimidine;
2,2'dihydroxy-3,5,6,3',5',6'hexachlorodiphenylmethene
2,2'dihydroxy-5,5'dichlorodiphenylmethane and their nontoxic acid addition salts.

Flavoring or sweetening materials of the type commonly employed in dentifrices may be included in the carrier. Such materials, if present, aid in modifying the particular tastes of the flavor in the manner desired. Examples of such additional materials include the flavoring oils, for example, oils of spearmint, peppermint, wintergreen, sassafras, clove, sage, eucalyptus, marjoram, cinnamon, lemon, and orange, as well as methylsalicylate. Suitable sweetening agents include sucrose, lactose, maltose, sorbitol, sodium cyclamate, and saccharine. Suitably, the flavor and sweetening agent may together comprise about 0.01 to 2.0 percent of the carrier.

The carrier suitably may contain a fluorine-containing compound having a beneficial effect on the care and hygiene of the oral cavity, for example, diminution of enamel solubility in acid and protection of the teeth against decay. Examples thereof include stannous fluoride, potassium stannous fluoride ($SnF_2.KP$), sodium hexafluorostannate, stannous chlorofluoride, sodium fluorozirconate, and sodium monofluorophosphate. These materials, which dissociate or release fluorine containing ions in water, suitably may be present in the carrier in an effective but nontoxic amount, usually within the range of about 0.01 to 1 percent of the water-soluble fluorine content thereof.

The following specific examples are further illustrative of the nature of the present invention, but it is to be understood that the invention is not limited thereto. The amounts and proportions in the specification and examples are by weight unless otherwise specified.

|  | Ex. 1 | Ex. 2 | Ex. 3 | Ex. 4 | Ex. 5 |
|---|---|---|---|---|---|
| Glycerine | 28.20 | 28.20 | 29.55 | 35.00 | 22.00 |
| Sodium carboxymethyl-cellulose | 0.80 | 0.80 | 0.70 | 0.70 | 0.70 |
| Sodium saccharin | 0.20 | 0.20 | 0.20 | 0.20 | 0.20 |
| Sodium benzoate | 0.50 | 0.50 | 0.50 | 0.50 | 0.50 |
| Distilled water | 15.00 | 15.00 | 17.00 | 12.00 | 21.45 |
| N-2-ethyl laurate potassium sulfo-acetamide | 1.50 | 1.50 | 2.00 | 1.50 | 1.50 |
| Monzyme AP neutral protease* | 0.25 | 0.25 | 0.25 | 0.25 | 0.25 |
| Calcium chloride | 0.50 | 0.50 | 0.50 | 0.50 | 0.50 |
| Bactopeptone** | 0.50 | 0.50 |  | 0.50 | 0.50 |
| Dicalcium phosphate dihydrate | 36.75 | 46.75 | 43.00 | 42.95 | 46.50 |
| Dicalcium phosphate anhydrous | 10.00 | 5.00 |  |  |  |
| Calcium carbonate | 5.00 |  | 5.00 | 5.00 | 5.00 |
| Flavor | 0.80 | 0.80 | 0.80 | 0.90 | 0.90 |
| Sodium caseinate |  |  | 0.50 |  |  |

*Monzyme AP neutral protease is a protease-amylase mixture of 4 parts protease (pH 7), 1 part protease (pH 10), and 1 part amylase manufactured by Monsanto.
**Bactopeptone is a polypeptide mixture derived by protein hydrolysis and is manufactured by Difco Laboratories.

The enzyme activity was determined using a Beckman Technicon amino acid autoanalyzer where activity is recorded in optical density units as a function of casein digestion and subsequent color development with trinitrobenzene sulfonic acid. All formulations were subjected to accelerated aging at 100° F for 3,6, and 9 weeks, and at each interval assayed for enzymatic activity in order to determine the efficacy of the compositions as enzyme dentifrices. After 9 weeks of accelerated aging all formulations had an enzymatic activity ranging from about 70 to 85 percent of the initial theoretically maximum activity. The formulations have also shown excellent cosmetic stability over a period of 9 weeks accelerated aging at 120° F.

What is claimed is:

1. A toothpaste formulation consisting of essentially of about 0.2 to 10 percent by weight of a gelling agent and about 20 to 75 percent by weight of a liquid vehicle proportioned to form a creamy mass, about 0.5 to 5 percent by weight of a water-soluble organic detergent, about 20 to 75 percent by weight of a dentally acceptable polishing agent, at least about 0.05 percent by weight of the neutral protease of Bacillus subtilis, and a stabilizer for retention of protease activity consisting essentially of about 0.1 to 0.5 percent by weight of a protein having an average molecular weight ranging from about 10,000 up to about 300,000 selected from the group consisting of partially hydrolized edible proteins and edible proteins and about 0.1 to 1.0 percent by weight of a group IIA metal ion salt.

2. The toothpaste of claim 1 in which the neutral protease is present in an amount of about 0.25 percent by weight and the protein is present in an amount of about 0.5 percent by weight.

3. The toothpaste of claim 1 in which the Group IIA metal ion is magnesium.

4. The toothpaste of claim 1 wherein said polishing agent is selected from the group consisting of dicalcium phosphate dihydrate, dicalcium phosphate anhydrous and calcium carbonate.

5. The toothpaste of claim 1 in which the neutral protease has an activity of at least about 0.02 Anson units per gram of formulation.

6. The toothpaste of claim 1 in which the protein is selected from the group consisting of partially hydrolyzed gelatin, partially hydrolyzed casein, and partially hydrolyzed collagen.

7. The toothpaste of claim 1 in which the Group IIA metal ion is supplied as a water-soluble, nontoxic salt.

8. The toothpaste of claim 5 in which the neutral protease has an activity of about 0.04 Anson units per gram of formulation.

9. The toothpaste of claim 1 in which said water-soluble organic detergent is N-2 ethyl laurate potassium sulfoacetamide.

* * * * *